United States Patent [19]

Shalati et al.

[11] Patent Number: 4,666,704

[45] Date of Patent: May 19, 1987

[54] CONTROLLED RELEASE DELIVERY SYSTEM FOR MACROMOLECULES

[75] Inventors: Mohamad D. Shalati, Richton Park, Ill.; Kallidaikurichi N. Sivaramakrishnan, Terre Haute, Ind.

[73] Assignee: International Minerals & Chemical Corp., Terre Haute, Ind.

[21] Appl. No.: 737,629

[22] Filed: May 24, 1985

[51] Int. Cl.$^4$ ............................................. A61K 31/74
[52] U.S. Cl. ........................................ 424/19; 424/22; 424/78; 424/DIG. 7; 514/2; 514/964; 514/965
[58] Field of Search ........................ 424/16, 19, 20, 22, 424/78, 83, DIG. 7; 514/2, 964, 965

[56] References Cited

U.S. PATENT DOCUMENTS

| | | | |
|---|---|---|---|
| 2,987,445 | 6/1961 | Levesque | 424/83 |
| 3,538,214 | 11/1970 | Polli et al. | 424/19 |
| 3,558,768 | 1/1971 | Klippel | 424/21 |
| 3,773,919 | 11/1973 | Boswell et al. | 424/78 |
| 3,835,221 | 9/1974 | Fulberth et al. | 424/20 |
| 4,127,127 | 11/1978 | Wong et al. | 128/260 |
| 4,148,871 | 4/1979 | Pitt et al. | 128/260 |
| 4,351,337 | 9/1982 | Sidman | 128/260 |
| 4,377,568 | 3/1983 | Chopra | 424/33 |
| 4,391,797 | 7/1983 | Folkman et al. | 424/19 |
| 4,459,279 | 7/1984 | Stricker et al. | 424/32 |

FOREIGN PATENT DOCUMENTS

| | | |
|---|---|---|
| 305498 | 2/1973 | Austria . |
| 0013131 | 7/1980 | European Pat. Off. . |
| 0052510 | 5/1982 | European Pat. Off. . |
| 637832 | 8/1983 | Switzerland . |
| 1417527 | 12/1975 | United Kingdom . |
| 2020181 | 11/1979 | United Kingdom . |
| 2025227 | 1/1980 | United Kingdom . |

OTHER PUBLICATIONS

Kallstrand et al., *Journal of Pharmaceutical Sciences*, vol. 72, No. 7, pp. 772–775, (Jul. 1983).

*Primary Examiner*—John Kight
*Assistant Examiner*—Nathan M. Nutter
*Attorney, Agent, or Firm*—Wendell R. Guffey; Thomas L. Farquer

[57] ABSTRACT

A controlled release implant composition which includes a core comprising a macromolecular drug and a water insoluble polymer and a homogeneous outer polymeric membrane formed by coating said core with an organic solution of a water insoluble polymer and a water soluble pore-forming agent.

20 Claims, No Drawings

CONTROLLED RELEASE DELIVERY SYSTEM FOR MACROMOLECULES

BACKGROUND OF THE INVENTION

This invention relates to an implant composition for the controlled release of macromolecular drugs. More specifically the present invention relates to a composition having a core comprising a biologically active macromolecular drug and a polymer and a homogenous polymer membrane coating containing a uniformly distributed water-soluble pore-forming agent.

The administration of therapeutic dosages of low molecular weight drugs has traditionally been accomplished by simple ingestion. Ingestion of macromolecular drugs, however, is not always feasible. Where low concentrations are loaded in a tablet, the rapid passage of materials through the body can render the tablets impracticable due to the number of tablets necessary to achieve the therapeutic dosage over time. When high concentrations are loaded, potentially harmful quantities can be released during the short residence period. In other cases the acidic environment of the stomach is destructive to the drug resulting in denaturization and/or acid hydrolysis.

Although some of these problems may be alleviated by implant methods of administration, the achievement of a substantially linear release of a macromolecular drug has yet to be accomplished. This can be attributed in part to difficulties in developing an effective rate limiting coating for the drug. Some research, however, has been directed toward perfecting controlled release systems.

U.S. Pat. No. 3,773,919 discloses a biodegradable controlled release composition having a core of a macromolecular antibiotic polypeptide, microencapsulated with polylactides and their glycolide copolymers. European Pat. No. 52 510 A2 similarly discloses microencapsulation of water soluble antibiotic polypeptides using synthetic biodegradable polymers such as polylactones and related polymers.

Biodegradable microencapsulation for the sustained release of enzymes, hormones, vaccines and other biologicals is discussed in Chang, *Journal of Bioengineering,* Vol. 1, pp. 25–32, (1976). Several examples of encapsulated water soluble proteins are disclosed therein, especially asparagine and insulin compositions.

In these references, diffusion of the core drug is dependent on the natural porosity of the polymer coating, subsequent pore formation in the coating due to polymer solubility and degradability, and in part on the solubility of the encapsulated drug.

Kallstrand et al., (1983) *Journal of Pharmaceutical Science,* Vol. 72, No. 7, pp. 772–775, describes a drug delivery system for controlling the diffusion rate which consists of a soluble tablet core surrounded by a porous membrane coating. The coating is formed by using a suspension of a water soluble pore-forming agent, e.g., sucrose, in an organic solution of a water insoluble polymer, e.g., an acetone solution of polyvinyl chloride. Sucrose's insolubility in the acetone solvent causes it to remain as a suspension of particulates in the polymer solution. Unfortunately, these particulates have a tendency to form larger aggregates when the coating is formed. When these aggregates are subsequently leached in an aqueous environment, a non-homogeneous pore structure results.

SUMMARY OF THE INVENTION

One important object of this invention is to provide a composition for releasing a biologically active macromolecular drug subcutaneously at a substantially constant rate with time.

Yet another object of this invention is to provide a macromolecular drug-delivery system fabricated from materials compatible with body tissue which can be prepared using conventional techniques without substantially affecting the desirable properties of the macromolecular drug.

In accordance with these objects, the present invention provides a composition suitable for implantation which provides controlled release of a macromolecular drug, said composition comprising (i) a core of the macromolecular drug and a water insoluble polymer, and (ii) a homogeneous pore-forming outer polymeric membrane, said membrane formed by coating said core with a solution of (a) an organic solvent, (b) a water insoluble high molecular weight polymer and (c) a water soluble pore-forming agent. In other aspects the present invention pertains to a method of preparing said composition and a method of treating animals using said composition.

DETAILED DESCRIPTION OF THE INVENTION

The invention broadly relates to a macromolecular drug-delivery system made from a drug/polymer core and a polymeric membrane coating which develops uniform porosity in an aqueous environment. The polymer in the core may function as a binder and/or an inert filler which supports the coating. The controlled release system of the present invention results in a substantially uniform, therapeutic daily dose of macromolecular drug even with drugs of low solubility. Accordingly, the composition of the present invention alleviates problems of erratic release of the macromolecular drug characteristic of prior art compositions.

The term "macromolecular drug" is used in its broadest sense in the present invention and is intended to include drugs, i.e. a substance that affects the activity of a specific bodily organ or function, having a molecular weight greater than about 2,000. Some drugs in this molecular weight range, e.g., steroids, anabolic agents and insulin, are characterized by a tendency toward aggregation with a resulting decrease in solubility. Suitable drugs include but are not limited to endocrine agents, chemotherapeutic agents, antibiotics, antidrug addiction agents, oncological treating agents, antifungal agents, anti-pulmonary disfunction agents, enzymes and macromolecular proteins affecting the central nervous system. Preferred macromolecular drugs include native and recombinant bioactive proteins and analogs thereof, such as (1) growth hormones and analogs thereof, (2) insulin and insulin-like growth factors such as somatomedins and analogs thereof and (3) other pituitory derived hormones such as prolactin, and analogs thereof. Particularly preferred macromolecular drugs include native porcine growth hormone and recombinant analogs thereof such as delta 7 (ser) porcine growth hormone produced by the process described in European Patent Office application No. 83305717.7 filed on Sept. 26, 1983 and published on Apr. 4, 1984 as Publication No. 0104920.

The core's water insoluble polymer provides a support structure for the macromolecular drug and may also act as a binder. The polymer may also function as a secondary control for drug release. The polymer can be selected both from biodegradable, bio-compatible polymers, such as polylactic acid, or from non-biodegradable, biocompatible polymers such as ethylene and vinyl acetate polymers and copolymers thereof having a vinyl acetate content of between about 10% and about 90% by weight. Where a biodegradable polymer is used, the rate at which the polymer degrades in physiological fluids is generally low in comparison to the rate at which the drug is dissolved. The available surface area of the drug therefore is dependent primarily on the extent of leaching within the core structure. Other biocompatible polymers useful in the present invention are ethylcellulose and polycaprolactone. Still other materials will be apparent to those skilled in this technology.

The relative quantity of drug and polymer selected for the core is not critical and generally is selected on a number of factors including the macromolecular drug employed, dose requirements, and size limitations of the composition. For example, it has been discovered that the cumulative release of a drug with time is greater at lower concentrations of the drug in the core. The aggregation of drug in the core that accompanies higher drug concentrations reduces the apparent solubility of the drug and therefore limits diffusion of the drug from the core.

A suitable core concentration for any specific drug can readily be determined by one skilled in the art using routine dose titration experiments. Generally, however, the core will contain from about 10% to about 90% by weight of drug. Often cores containing from about 30% to about 70% by weight of drug are preferred.

Several known methods of core formation may be used in the present invention, such as pelletizing a dry mixture of drug and polymer using the compression equipment disclosed in U.S. Pat. No. 2,987,445; and molding a gel-like solution of dissolved polymers followed by vacuum drying to form a polymer matrix, as disclosed in Langer et al. (1976) *Nature*, 263: 797–799, and the present invention is not limited to any specific techniques. In the pelletization procedure, composite particles of the macromolecular drug and polymer may be prepared by freeze-drying a suspension of drug particles in an organic solution of the polymer. The composite, freeze-dried particles then are pressed into pellets using available compression equipment. The shape of the core, herein referred to as a pellet, is not critical and any configuration suitable for implantation may be used.

In the present invention, the controlled delivery of a macromolecular drug at a substantially constant rate (linear rate) results primarily from the unique physical characteristics of the polymeric coating membrane surrounding the core. The implant composition of the present invention utilizes a coating of a water insoluble, high molecular weight polymer having a water soluble pore-forming agent uniformly or homogeneously distributed therein. Excellent distribution of the pore-forming agent in the coating is obtained because a pore-forming agent is used which is soluble both in the organic solvent used to apply the coating and in the aqueous fluids encountered upon implantation. Mutual solubility of the pore-forming agent in both the organic solvent and water is a key and essential feature of the present invention. Dissolution of the pore-forming agent after implantation produces a uniform dispersion of microporous channels through the polymeric coating membrane. This uniform channel structure contributes to a uniformity in drug release from the core.

The polymeric membrane coating is made from water insoluble, bio-compatible polymers. Suitable materials include polylactic acid, ethylcellulose, polycaprolactone, and polymethylacrylate. Still other materials suitable for the polymeric coating will be recognized by those skilled in the art.

The coating preferably is made from a polymer of high molecular weight (greater than 2000). Such polymers exhibit properties of increasing mechanical durability as molecular weight increases. Molecular weights in excess of about 10,000 however, offer few additional benefits.

The pore-forming agent is selected on the basis of its biocompatibility, its solubility in organic solvents, and its solubility and rate of dissolution in water. When a water soluble, pore-forming agent, such as sucrose, is used in combination with an organic polymer solution in which such agent is not soluble, the agent has a tendency to aggregate thereby preventing a uniform distribution of the pore-forming agent within the subsequently formed coating membrane. When the pore-forming agent is subsequently dissolved from the non-homogeneous coating membrane after implantation, a non-uniform channel structure is produced which often results in erratic release of the macromolecular drug from the implant. By using a proper combination of pore-forming agent and organic solvent, such that the pore-forming agent is soluble in both water and the organic solvent used to prepare the coated drug (implant), the present invention avoids the above-noted problem encountered with the prior-mentioned procedure and composition and results in a homogeneous, pore-forming outer polymeric membrane.

Low molecular weight pore-forming agents, generally defined as a molecular weight of less than about 2000 and preferably less than about 1000, exhibit a more rapid rate of dissolution than higher molecular weight compounds. As the controlled release of the drug is dependant on diffusion through the pores of the coating membrane, rapid dissolution of the pore-forming agent is a desirable characteristic.

Pore-forming agents suitable for use in the present invention include dimethyl and diethyl tartrate, lower partial esters of citric acid, such as mono- and diethyl citrate, and, esters of citric acid such as trimethyl citrate. These agents exhibit the required co-solvency in both the organic coating solvent and the aqueous fluids encountered upon implantation. Other pore-forming agents suitable for the present invention will be apparent to those skilled in the art.

The pore-forming agent can be added to the coating formulation in a range of from about 1% to about 60% by weight of the coating polymer. The addition of dimethyl tartrate, for example, in a concentration range of between about 20% and about 50% by weight of coating polymer has provided good results. Generally, a higher concentration of pore-forming agent creates a more porous coating and therefore a higher release rate. Commonly recognized organic solvents for co-dissolving the coating membrane polymer and pore-forming agent having a sufficient volatility for use in the present invention include, but are not limited to hydrocarbons, chlorinated hydrocarbons, ethers, esters, ketones, alcohols and the like. Specific examples of solvents include toluene, ethyl acetate, acetone, methylene chloride, and ethyl alcohol. The solvent merely serves as a vehicle for applying the coating and is removed from the composition for example by evaporation.

The coating solution may be applied to the core of the composition and the solvent evaporated by techniques commonly employed in the art. Uniform spraying of batches of cores in a fluidized bed, for example, is disclosed in Goodhart et al., (1984) *Pharmaceutical Technology*, pp. 65–71. Any other method generally recognized in the art for controlled homogeneous coating also is acceptable. The method of applying the coating to the core is not critical.

The rate of release of a drug from the implant will be dependent on the concentration of pore-forming agent in the coating and on the overall thickness of the coating. The rate of release will generally vary directly with the concentration of pore-forming agent and inversely with the thickness of the coating. As noted earlier, the concentration of the drug in the core also is a factor. The choice of appropriate parameters is within the skill of the art.

Since coatings applied by conventional spray technology are subject to wide variations in total weight due to fluctuations in ambient conditions, environmental controls may be necessary to ensure uniform quality. The choice of coating techniques and processing conditions for any such technique is easily within the skill of art.

The compositions of this invention may be administered to an animal employing any of the known implantation techniques, such as subcutaneous, intramuscular, and intraperitoneal implantation or by injection into a body fat deposit. Preferably, the implant composition is subcutaneously implanted in an animal employing any art-recognized technique. Animals may be retreated with the implant composition from time-to-time, depending on the specific drug employed. Animals which are treated in this manner include, without limitation, mammals such as cattle, sheep, goats, swine and the like and birds such as poultry.

Specific examples illustrative of the invention composition and method of preparation are described below and are not intended to limit the scope of the invention.

EXAMPLE 1

In this example a composition containing the macromolecular drug lysozyme was shaped to form a solid cylindrical core and sprayed with a suitable solution of ingredients to form a homogeneous polymeric membrane coating.

Lysozyme was dissolved in deionized water at a concentration of 10 mg/ml and was adjusted to a pH of 7.4 using dilute HCl. The solution then was filtered, sterilized and lyophilized. The lyophilized solid was mixed with deionized water keeping the protein to water weight ratio at about 55:45 and was again lyophilized. The powder obtained was suspended in an acetone solution of polylactic acid (molecular weight of about 50,000). The acetone was evaporated at room temperature in a vacuum desiccator to give a crude particulate mixture (composite) of lysozyme and polylactic acid. The mixture then was pelletized in a Stokes machine to produce cylindrical pellets each weighing about 110 mg and measuring 4.0 mm in diameter and approximately 8.1 mm in length.

Pellets then were placed at the tip of a flat, hollow needle and held in place with a vacuum. The needle assembly was connected to a motor which rotated the assembly and thereby exposed the complete surface of the pellet to a sprayer.

A coating solution was prepared by dissolving polylactic acid in acetone to give a 3% by weight solution. Dimethyl tartrate, as the pore-forming agent then was dissolved in the polylactic acid-acetone solution. This acetone solution of polylactic acid and dimethyl tartrate was sprayed on the pellets by using a Paasche air-brush for various time periods in order to apply different coating thicknesses to the core.

EXAMPLE 2

Modifications in the concentration of drug in the core, coating time (i.e., coating thickness) and the concentration of pore-forming agent in the coating all affect the ultimate release rate of the macromolecular drug. Table 1 below illustrates drug release data from a composition prepared using a preferred set of conditions. The Table shows the drug release data for a composition having a core, containing 60% by weight lysozyme and 40% polylactic acid, coated with an acetone solution of polylactic acid and dimethyl tartrate as the pore-forming agent. The coating solution contained 41% by weight of dimethyl tartrate. The coating was applied using the procedure described in Example 1. As indicated, a consistent, substantially linear release rate of the drug was obtained for about a two week period starting at about day 6.

Because the controlled release of drug is largely dependent upon the water solubility of the pore-forming agent and therefore on the availability of sufficient aqueous solvent, the placement of the composition in the body will greatly affect the degree of pore development with time. As such, cumulative release data for the first two to five days may be initially misleading due to incomplete pore formation.

TABLE 1

| | RELEASE DATA | | |
|---|---|---|---|
| Elapsed Time (Days) | mg Released Day | Cumulative mg Released | Cumulative % Released |
| 1.03 | 1.00 ± 1.85 | 1.04 | 1.57 |
| 2.04 | 1.82 ± 2.94 | 2.87 | 4.34 |
| 3.05 | 3.06 ± 2.50 | 4.95 | 7.50 |
| 4.30 | 1.74 ± 1.58 | 7.14 | 10.81 |
| 5.23 | 1.61 ± 1.27 | 8.64 | 13.09 |
| 5.91 | 1.45 ± 0.89 | 9.63 | 14.59 |
| 6.79 | 1.45 ± 0.83 | 10.91 | 16.52 |
| 7.68 | 1.73 ± 0.96 | 12.45 | 18.85 |
| 8.66 | 1.48 ± 0.60 | 13.91 | 21.05 |
| 9.66 | 1.47 ± 0.38 | 15.38 | 23.28 |
| 10.83 | 1.52 ± 0.23 | 17.15 | 25.96 |
| 11.88 | 1.57 ± 0.17 | 18.80 | 28.46 |
| 12.69 | 1.61 ± 0.13 | 20.10 | 30.42 |
| 13.68 | 1.49 ± 0.17 | 21.58 | 32.65 |
| 14.68 | 1.50 ± 0.17 | 23.07 | 34.91 |
| 15.63 | 1.34 ± 0.24 | 24.35 | 36.85 |
| 16.70 | 1.22 ± 0.24 | 24.66 | 38.83 |
| 17.66 | 1.21 ± 0.20 | 26.83 | 40.60 |
| 18.74 | 1.16 ± 0.25 | 28.08 | 42.50 |
| 19.67 | 1.08 ± 0.25 | 29.08 | 44.01 |
| 20.67 | 0.91 ± 0.19 | 29.99 | 45.38 |
| 21.77 | 0.81 ± 0.18 | 30.88 | 46.74 |
| 22.67 | 0.74 ± 0.12 | 31.55 | 47.76 |
| 23.68 | 0.65 ± 0.13 | 32.21 | 48.76 |
| 24.75 | 0.57 ± 0.11 | 32.82 | 49.68 |
| 25.68 | 0.53 ± 0.10 | 33.31 | 50.43 |
| 26.68 | 0.48 ± 0.09 | 33.79 | 51.15 |
| 27.68 | 0.66 ± 0.05 | 34.45 | 52.16 |
| 28.62 | 0.61 ± 0.03 | 35.02 | 53.02 |
| 29.64 | 0.44 ± 0.11 | 35.47 | 53.70 |
| 30.61 | 0.47 ± 0.02 | 35.93 | 54.40 |
| 31.75 | 0.40 ± 0.10 | 36.39 | 55.10 |
| 32.76 | 0.36 ± 0.10 | 36.75 | 55.65 |

TABLE 1-continued

RELEASE DATA

| Elapsed Time (Days) | mg Released Day | Cumulative mg Released | Cumulative % Released |
| --- | --- | --- | --- |
| 33.61 | 0.33 ± 0.08 | 37.03 | 56.08 |
| 34.60 | 0.36 ± 0.03 | 37.39 | 56.62 |

After extensive testing, it has been found that cores coated on the same day with similar concentrations of macromolecular drug, similar coating spray times, and similar concentrations of pore-forming agent in the coating have shown excellent reliability.

EXAMPLE 3

Using the procedure and materials set forth in Example 1, a five-fold decrease in cumulative percent release (after about 24 days) was obtained when the concentration of lysozyme in the core was increased from about 45% to about 75% by weight. The cumulative release decreased from about 37.8% to about 7.4%. In these tests, the coating time was fixed at 120 seconds, and dimethyl tartrate was used as the pore-forming agent at a concentration of 35% by weight in a polylactic acid-acetone solution.

EXAMPLE 4

Using the procedure and materials set forth in Example 1 with the exception of using a 60% concentration of lysozyme in the core and a 25% concentration of dimethyl tartrate as the pore-forming agent in the coating, coating time was increased from 42 seconds to 90 seconds. After 23 days of testing the thinner coating (42 seconds coating time) exhibited a cumulative release of 62% in comparison to the thicker coating (90 seconds coating time) which exhibited a cumulative release of 45%.

EXAMPLE 5

A controlled release composition was produced in accordance with the process and materials set forth in Example 1. Using a 60% concentration of lysozyme and a 90 second coating time, an increase in the concentration of pore-forming agent from 25% by weight to 41% by weight resulted in an increase in the cumulative release percentage (after about 30 days) of from about 30% to about 54%.

Since variations of this invention will be apparent to those skilled in the art, it is intended that the invention be limited only by the scope of the appended claims.

We claim:

1. An implant composition which provides controlled release of a macromolecular drug at a substantially constant rate, said composition comprising
a core of the macromolecular drug and a water insoluble polymer; and
a homogeneous pore-forming outer polymeric membrane having a uniform distribution of pore-forming agents, said membrane formed by coating said core with a homogeneous solution of (a) an organic solvent, (b) a water insoluble high molecular weight polymer and (c) water soluble pore-forming agent.

2. The composition of claim 1 wherein said macromolecular drug is a native or recombinant bioactive protein or an analog thereof.

3. The composition of claim 2 wherein said protein is native porcine growth hormone or a recombinant analog thereof.

4. The composition of claim 1 wherein said macromolecular drug has a molecular weight of at least about 2000.

5. The composition of claim 1 wherein said core polymer is selected from the group consisting of polylactic acid, ethylcellulose, and polycaprolactone.

6. The composition of claim 1 wherein said water soluble pore-forming agent is selected from the group consisting of dimethyl tartrate and diethyl tartrate.

7. The composition of claim 1 wherein said water insoluble, high molecular weight polymer in said polymeric membrane is selected from the group consisting of polylactic acid, ethylcellulose and polycaprolactone.

8. A method of preparing an implant composition which provides controlled release of a macromolecular drug at a substantially constant rate which comprises:
(a) forming a mixture of said macromolecular drug and a water insoluble polymer into a pellet;
(b) coating said pellet with a homogeneous solution of (i) an organic solvent, (ii) a water insoluble high molecular weight polymer and (iii) a water soluble pore-forming agent; and
(c) evaporating said organic solvent thereby forming an outer polymeric membrane having a uniform distribution of pore-forming agents.

9. The method of claim 8 wherein said macromolecular drug is a native or recombinant bioactive protein or an analog thereof.

10. The method of claim 9 wherein said protein is native porcine growth hormone or a recombinant analog thereof.

11. The method of claim 8 wherein said macromolecular drug has a molecular weight of at least about 2000.

12. The method of claim 8 wherein said core polymer is selected from the group consisting of polylactic acid, ethylcellulose, and polycaprolactone.

13. The method of claim 8 wherein said water soluble pore-forming agent is selected from the group consisting of dimethyl tartrate and diethyl tartrate.

14. The method of claim 8 wherein said water insoluble, high molecular weight polymer in said polymeric membrane is selected from the group consisting of polylactic acid, ethylcellulose and polycaprolactone.

15. A method of treating an animal with the controlled release composition of claim 1 wherein said composition is subcutaneously implanted in said animal.

16. A method of treating an animal with the controlled release composition of claim 2 wherein said composition is subcutaneously implanted in said animal.

17. A method of treating an animal with the controlled release composition of claim 3 wherein said composition is subcutaneously implanted in said animal.

18. A method of treating an animal with the controlled release composition of claim 4 wherein said composition is subcutaneously implanted in said animal.

19. A method of treating an animal with the controlled release composition of claim 6 wherein said composition is subcutaneously implanted in said animal.

20. A method of treating an animal with the controlled release composition of claim 7 wherein said composition is subcutaneously implanted in said animal.

* * * * *